United States Patent [19]

Klun et al.

[11] 4,216,202

[45] Aug. 5, 1980

[54] SEX ATTRACTANT FOR CORN EARWORM MOTHS

[75] Inventors: Jerome A. Klun, Potomac; Jack R. Plimmer, Columbia, both of Md.; Alton N. Sparks, Tifton, Ga.; Barbara B. Leonhardt, Potomac, Md.

[73] Assignee: The United States of America as represented by the Secretary of Agriculture, Washington, D.C.

[21] Appl. No.: 25,136

[22] Filed: Mar. 29, 1979

[51] Int. Cl.$^2$ .................................. A01N 17/14
[52] U.S. Cl. .................................. 424/84
[58] Field of Search .................................. 424/84

[56] References Cited

PUBLICATIONS

J. Economic Entomology 68, pp. 603–604, (1975).

Primary Examiner—Allen J. Robinson
Attorney, Agent, or Firm—M. Howard Silverstein; William E. Scott; David C. McConnell

[57] ABSTRACT

A combination of (Z)-11-hexadecenal and (Z)-9-hexadecenal is an effective attractant for adult male corn earworm moth.

3 Claims, No Drawings

SEX ATTRACTANT FOR CORN EARWORM MOTHS

BACKGROUND OF THE INVENTION

1. Field of the Invention

This invention relates to insect attractants and more specifically to a highly effective attractant for the corn earworm.

2. Description of Prior Art

Attractants for some insect species are known in the art. For example, hexalure, cis-7-hexadecen-1-ol acetate is an effective attractant for adult male pink bollworm moths, *Pectinophora gossypiella* (Saunders). However, propylure, the sex pheromone isolated from virgin pink boll-worm moths failed to attract the male pink bollworm in the field (Science 152,1516–17, 1966). In fact, (Z)-11-hexadecenal, one of the components of the attractant of this invention was found to inhibit the catch of male corn earworm adults by virgin females of the same species (J. Econ. Entomology 68, 603–4, 1975). As little as 5 mg of (Z)-11-hexadecenal resulted in 50% inhibition of male catch by four virgin females while 50 mg inhibited the catch in excess of 99%.

BRIEF SUMMARY OF THE INVENTION

An object of this invention is to provide an attractant for adult male corn earworm moths.

A further object is to provide a method of attracting and trapping adult male corn earworm moths.

A still further object is to provide a means of interfering with mating communication of corn earworm moths and thereby suppress the population of the moths.

Still another object is to provide a means to detect infestations of the corn earworm, to delineate infested areas, and to estimate corn earworm population densities.

In general, according to this invention, a novel combination of (Z)-11-hexadecenal and (Z)-9-hexadecenal is found to be an effective attractant for adult male corn earworm moths. The new attractant can be used to bait a trap or it can be used to suppress corn earworm populations by permeating the atmosphere in an infected area. The latter interferes with mating communication causing substantial disruption of mating and consequent reduction in insect population.

DESCRIPTION OF THE INVENTION

Many major insect pests infest corn, cotton, tobacco and other crops and their larvae cause considerable economic loss, to the extent that cultivation of these crops may not be possible in certain areas. Chemical pesticide sprays have been used to control the insects responsible for crop damage for many years, but the intensive use of conventional chemicals may ultimately present hazards to man and the environment and it has frequently resulted in the survival of insecticide-resistant insect populations that can no longer be treated effectively. Therefore, insecticidal chemicals should be used only when the population of pest species rises to levels that could result in substantial economic loss. Methods of pest control that offer an alternative to the use of conventional chemicals are needed.

Females of many lepidopteran species attract males by emitting a sex attractant pheromone. If the active component(s) of the pheromone can be isolated and identified, this material can be used as a lure in an insect trap to attract and catch male moths. The pheromone is slowly vaporized from a suitable formulation and the male moth enters the trap where it is held or killed. If such traps are situated in the area in which an infestation of moths may occur, the presence of moths can then be detected. Thus, the application of pesticides can be delayed until the number of insects in the traps reaches a predetermined level when crop damage might occur. Pheromones may also be used to attract male insects to traps or alternative locations in sufficient numbers to interrupt the reproductive cycle and reduce the numbers of pests in subsequent generations.

A further application of insect sex pheromones or attractants is their use to suppress insect populations in infested areas by interfering with mating communication. If the air throughout the area is permeated with the compounds, substantial mating disruption may result, with a consequent reduction in insect population.

The corn earworm, *Heliothis zea* (Boddie), is one of the major pests of crops in the United States. The sex pheromone system of this insect contains chemicals that are potent attractants for the male and thus provide a powerful system for population monitoring and permit mating disruption programs for this insect. We have identified the active compounds as (Z)-9-hexadecenal and (Z)-11-hexadecenal.

Various materials and methods are employed to extract, isolate, and identify the active compounds in the pheromone of the female corn earworm and to test the male behavioral responses to the synthetic compounds. Although the compounds have been synthesized previously, we found that the presence of impurities rendered them ineffective and for the purposes of this invention they must be at least 99% pure.

MATERIALS AND METHODS

Pupae were obtained from cultures of H. zea at the USDA Laboratory at Tifton, Georgia and were separated by sex. Female pupae were isolated and held under constant light at 22°–26° C. Adult females were held 1 to 4 days after emergence. Pressure exerted on the abdomen of the insect caused forcible eversion of the ovipositor, which was carefully excised through the tergum of the 8th abdominal segment anterior to the ovipore. The cut surface of the excised ovipositor tip was placed briefly on filter paper to absorb hemolymph, and the tip was then placed in a specially designed micro vial containing an internal standard (4ng.(Z)-11-tridecenyl acetate) and heptane (3 $\mu$l). A description of the micro vial is found in J. Chem. Ecology 3, 447–459, 1977 and is considered to be incorporated into this specification.

The heptane extract (3 $\mu$l) was analyzed on a gas chromatograph equipped with a microprocessor-controlled splitless injector system and a flame ionization detector (Hewlett-Packard Model 5840A). The carrier gas used was helium, flow rate 2 ml./min at 120° C. column temperature, injector temperature 225° C. The injector was purged 1.1 minutes after injection. The column was temperature-programmed; 120° C. at injection held for 2 minutes, then heated at 30°/min to 180° C. (polyethylene glycol-20M-nitroterephthalic, Supelco SP1000 column) or to 200° C. (methyl silicone fluid, Supelco SP2100 column). The columns used were glass open-tubular capillary (60 m×0.2 mm id) coated with either SP1000 or SP2100.

Mass spectra were obtained with a combined gas chromatograph-mass spectrometer (Finnigan Model 4000), equipped with a data system (Finnigan 6110 Data System). The gas chromatograph of the mass spectrometer was equipped with a SP2100 wall-coated open tubular glass capillary column (20 m×0.25 mm I.D.) that could be operated in the splitless mode. The total volume of the column effluent was admitted to the mass spectrometer source.

Behavioral response assays were conducted in cylindrical screened cages (13.5 cm×7 cm O.D.). Air from an outside source was pumped through a 10.3 cm tube and delivered at 1.5–1.8 m/sec flow rate. Males were obtained from laboratory cultures and held in a 16:8 LD (light to dark) regime at 26° C. for 3 to 5 days after emergence from pupae. Sets of 8 to 10 adult males were held at 20 C in cages for each bioassay, which consisted of a 30 sec. exposure to a chemical stimulus on the tip of a disposable glass pipet held 4 cm upwind of the cage. Airflow downwind was exhausted through the vent of a laboratory fume food. Each test was scored by the number of males that responded to the stimulus with wing vibration, extension of scent brushes and genitalia, and clasper responses within the 30 seconds exposure to the stimulus.

Field tests were conducted in cornfields in Antigua, West Indies, and Tifton, Georgia, USA, when the corn was at the silking state of development. Each trap was constructed of 2 plastic plates, 25 cm diameter and 2.5 cm apart; the upper surface of the bottom plate was coated with a commercially available substance for holding the trapped insects. One of the substances which we used was Stickem Special, a combination of 40 parts polymerized 1-butene, 35 parts polymerized 2-methyl propene, and 14 parts polymerized butane, in paraffin wax. Any other available product to which the insects would stick and be held in a trap is suitable for the purposes of this invention. The plates were separated by a centrally positioned cylinder formed from hardware cloth. The traps were deployed on wire fences around the perimeter of the cornfield at 15 m intervals and 1.5 m above the ground in a randomized complete-block design with 6 to 9 replicates.

The chemicals and combinations to be tested were dissolved in 10 to 20 $\mu$l of heptane and were dispensed onto 1.5 cm lengths of cotton dental roll. The cotton rolls were placed on the sticky surface near the center of the lower plate of the trap. Each roll was removed before 10.00 a.m. and replaced with new treated rolls about one hour before sunset each day.

Check traps were baited with three 2 to 7 day old females contained in a cylindrical cage that fitted into the hardware cloth cylinder used as a trap spacer. The female moths were obtained from the USDA, Tifton, Georgia Laboratory culture.

ISOLATION AND IDENTIFICATION OF THE ACTIVE COMPOUNDS

Corn earworm ovipositor wash (3 $\mu$l, one female equivalent) was injected into the gas chromatograph operated in the splitless injection mode. The major component, (Z)-11-hexadecenal, has previously been identified as a component of the sex pheromone (J. Econ. Entomology 68, 603–4, 1975). This compound was well resolved from hexadecanal and other hexadecenals. On this column, minor components (Z)-7-hexadecenal and (Z)-9-hexadecanal appeared as two distinct peaks but were not completely resolved. The identity of the compounds was indicated by their retention times, which were identical with those of authentic compounds on both SP1000 and SP2100 columns. When a sample of the extract was shaken with 2,4-dinitrophenylhydrazine and reexamined by gas chromatography, peaks due to the above aldehydic compounds were absent, confirming that they possessed carbonyl groups.

For mass spectrometry, a heptane solution (20 to 30 female equivalents) was injected into the gas chromatograph inlet of the mass spectrometer. The reconstructed gas chromatography (rgc) based on total ion current showed 3 peaks. The first peak had the following major ions: $M^+$ at m/e 238, and $M^+$-18 at m/e 220.

The base peak was at m/e 55. The major component had a similar mass spectrum. The mass spectrum and retention time of the first peak was consistent with (Z)-9-and/or (Z)-7-hexadecenal. That of the second peak was consistent with (Z)-11-hexadecenal. The third peak had $M^+$ $-18$ at m/e 222 and the base peak was at m/e 55. The molecular ion $M^+$ at m/e 240 was too weak to be detected but the fragmentation pattern indicated that the compound was n-hexadecenal.

Because the peak corresponding to (Z)-9- and (Z)-7-hexadecenals was unresolved on the gas chromatograph-mass spectrometer, conversion to the epoxides with m-chloroperbenzoic acid was used to further obtain information. The fragmentation patterns of epoxides often contain intense peaks that reveal the location of the epoxide function. The ovipositor wash (50 to 100 female equivalents) was epoxidized and injected onto the gas chromatograph. The major component had a spectrum typical of a 16-carbon epoxyaldehyde. The large peak at m/e 197 formed by $\alpha$-cleavage (J.A.O.C.S. 51, 466–469, 1974) confirmed that it was an 11,12-epoxy-hexadecanal. The mass spectrum of a shoulder at the leading edge of this peak contained fragment ions at m/e 141 and m/e 169, which would be expected from 7,9- and 9,10-epoxy-hexadecanal respectively. The retention times indicated that these compounds had a cis configuration.

TESTING MALE BEHAVIORAL RESPONSES

Laboratory behavioral assays: Combinations of synthetic materials, purified as described later were tested in the laboratory as described above under Materials and Methods. For bioassay a set of 10 males in a screened cage positioned in a 20°–22° C. airflow (1.5–1.8 m/sec) was exposed to the stimulus on the surface of a glass tube held 4 cm upwind of the caged moths for 30 seconds. The number of males that responded to the stimulus with wing vibration, extension of genitalia, and clasper response in the 30 second exposure period was recorded; the test was conducted in a randomized complete-block design with ten replicates. In each replicate a separate set of 10 caged males was exposed to each treatment. Thus, about 100 males (in sets of ten) were exposed to each stimulus. The percentage male response indicates the number of males that responded to each stimulus during a 30 second exposure. Each set of 10 males was exposed to only one stimulus and then discarded.

Table 1 shows the percentage male response to treatments: the number of males that respond by wing vibration, extension of genitalia and clasper response was recorded. A mixture of (Z)-11-, (Z)-7-, and (Z)-9-hexadecenal was as active as the mixture of all four components and a mixture of (Z)-11-and (Z)-9-hexadecenal (57.5 ng+1.13ng) was almost as active as all four components.

Field tests: These were conducted as described above under Materials and Methods. The results paralleled those of the laboratory bioassay and are shown in Table 2. Combinations of (Z)-11-hexadecenal and (Z)-9-hexadecenal were necessary for male attraction at two different geographic locations. Mixtures containing 115 µg of (Z)-11-hexadecenal and 2.25 µg of (Z)-9-hexadecenal were the most effective among the combinations of the four ovipositor wash components used. A mixture containing (Z)-11-hexadecenal, (Z)-9-hexadecenal, (Z)-7-hexadecenal, and hexadecanal captured as many males as four virgin females in tests in Georgia.

When 238 g of an attractant mixture containing (Z)-11-, (Z)-9- and (Z)-7-hexadecenal (231 µg, 4.5 µg and 2.6 µg, respectively) was tested in Antigua it caught as many males as three virgin female moths (Table 3). The presence of chemical impurities in the attractant mixture rendered the lure ineffective. Evidence from data obtained at this time indicates that the impurities are aldehyde oxidation products.

PURIFICATION OF SYNTHETIC COMPOUNDS

The compounds present in the ovipositor wash can be purchased commercially or synthesized by methods described in the chemical literature. Before use we purified them to greater then 99.9% purity as indicated by glc analysis on the SP1000 chromatographic column.

Final purification was achieved by high pressure liquid chromatography on silica treated with silver nitrate (J. Chromatographic Science 15, 10–13, 1977). The effluent from the high pressure liquid chromatograph, containing the desired compound, was collected into a reservoir containing the antioxidant, 2,6-di-tert-butyl-4-methyl phenol. An antioxidant is used to prevent formation of undesirable products of oxidation and to help the compounds return their original biological efficacy. Other than stabilizing the compounds and the combinations of compounds, the antioxidant does not enhance their effetiveness. The solvent in which the compounds and combinations of compounds were dissolved prior to dispensing on the cotton rolls for use in the traps contained 5 µg/µl of antioxidant.

Table 1

Male *Heliothis zea* sex stimulation responses in laboratory assays to combinations of aldehydes identified from the female ovipositor.[1]

| Treatment | ng Stimulus | Percentage male response[2] |
|---|---|---|
| I | 57.5 Z-11 | 9.9 c |
| II | 57.5 z-11 + 0.65 Z-7 | 16.5 c |
| III | 57.5 Z-11 + 1.13 Z-9 | 62.4 ab |
| IV | 57.5 Z-11 + 0.65 Z-7 + 1.13 Z-9 | 78.9 a |
| V | 57.5 Z-11 + 0.65 Z-7 + 1.13 Z-9 + 2.75 $C_{16}$ | 73.6 a |
| VI | 57.5 Z-11 + 0.65 Z-7 + 2.75 $C_{16}$ | 12.6 c |
| VII | 57.5 Z-11 + 1.13 Z-9 + 2.75 $C_{16}$ | 52.8 b |
| VIII | 57.5 Z-11 + 2.75 $C_{16}$ | 7.5 c |

[1]Z-11, Z-9, and Z-7 are Z-11-hexadecenal, Z-9-hexadecenal, and Z-7-hexadecenal, respectively. $C_{16}$ is hexadecenal.
[2]Means followed by the same letter are not significantly different from other at P = 0.05 according to Duncan's new multiple range test.

Table 2

Male *Heliothis zea* sex attraction field responses to synthetic mixtures of $C_{16}$ aldehydes identified from heptane washes of the female ovipositor.[1]

| Treatment[2] | µg Stimulus | $\bar{x}$ males trap[3] | Total males trapped[4] |
|---|---|---|---|
| I | 115 Z-11 | 1.7 c | 4 |
| II | 115 Z-11 + 1.3 Z-7 | 0.09 c | 2 |
| III | 115 Z-11 + 2.25 Z-9 | 13.9 b | 63 |
| IV | 115 Z-11 + 1.3 Z-7 + 2.25 Z-9 | 12.6 b | 40 |
| V | 115 Z-11 + 1.3 Z-7 + 2.25 Z-9 + 5.5 $C_{16}$ | 18.4 ab | 47 |
| VI | 115 Z-11 + 1.3 Z-7 + 5.5 $C_{16}$ | 3.6 c | 2 |
| VII | 115 Z-11 + 2.25 Z-9 + 5.5 $C_{16}$ | 15.0 b | 35 |
| VIII | 115 Z-11 + 5.5 $C_{16}$ | 1.4 c | 0 |
| IX | unbaited trap | — | 0 |
| X | 4 virgin females | 25.6 a | — |

[1]Z-11, Z-9, Z-7 are Z-11-hexadecenal, Z-9-hexadecenal, and Z-7-hexadecenal, respectively. $C_{16}$is hexadecenal.
[2]All treatments were evaporated from cotton wicks.
[3]Eight replicates over 6 consecutive nights 8/8–13/78 Tifton, Georgia. Means followed by the same letter are not significantly different from each other (P = 0.05).
[4]Nine replicates over 3 consecutive nights 3/3–3/5/78 Antigua Island.

Table 3

Male *Heliothis zea* sex attraction responses to 3 virgin females 1–7 days old, to a lure containing 0.2% impurity, and to a lure containing 2% impurity.

| Stimulus | Males/trap[1] |
|---|---|
| 3 Virgin females | 25.2 |
| 231 µg Z-11 + 2.6 µg Z-7 + 4.5 µg Z-9 (less than 0.2% chemical impurity) | 24.8 |
| 231 µg Z-11 + 2.6 µg Z-7 + 4.5 µg Z-9 + 11 µg $C_{16}$ (2% chemical impurity) | 2.6 |

[1]Nine replicates, 1 night trapping

We claim:

1. An attractant for the adult male corn earworm moths comprising an effective amount of an effective attractant combination of (Z)-11-hexadecenal and (Z)-9-hexadecenal, said components being at least 99.0% pure, and combined at a ratio of about 115 to 2.25 on a weight basis, and an effective antioxidant amount of 2,6-di-tert-butyl-4-methyl phenol.

2. A method of attracting adult male corn earworm moths comprising baiting a trap with an effective attractant amount of an effective attractant combination of (Z)-11-hexadecenal and (Z)-9-hexadecenal, said components being at least 99.0% pure, and combined at a ratio of about 115 to 2.25 on a weight basis, and an effective antioxidant amount of 2,6-di-tert-butyl-4-methyl phenol.

3. A method of suppressing the population of corn earworms in infected areas comprising permeating the atmosphere in said area with an effective attractant amount of an effective attractant combination of (Z)-11-hexadecenal and (Z)-9-hexadecenal, said components being at least 99.0% pure, and combined at a ratio of about 115 to 2.25 on a weight basis, and an effective antioxidant amount of 2,6-di-tert-butyl-4-methyl phenol.

* * * * *